United States Patent [19]

Murphy et al.

[11] 4,337,859
[45] Jul. 6, 1982

[54] METHOD OF PRODUCING A COSMETIC PRODUCT CONTAINING A POWDER CAKE

[75] Inventors: John H. Murphy, Matamoras; John J. Brodzinski, Milford, both of Pa.; Donald D. Horton, Glen Spey, N.Y.

[73] Assignee: Kolmar Laboratories Inc., Port Jervis, N.Y.

[21] Appl. No.: 142,447

[22] Filed: Apr. 21, 1980

[51] Int. Cl.³ ............... A45C 11/00; A45D 33/00; B65B 1/04; B65B 5/00

[52] U.S. Cl. ............................... 206/37; 53/242; 132/82 H; 132/83 R; 206/823

[58] Field of Search ............... 206/37, 525, 823; 132/82 H, 83 R; 53/242

[56] References Cited

U.S. PATENT DOCUMENTS

| | | | |
|---|---|---|---|
| 1,462,034 | 7/1923 | Finlayson | 132/82 H |
| 1,609,290 | 12/1926 | Brodrick | 206/823 |
| 1,652,755 | 12/1927 | Brodrick | 206/823 |
| 2,158,099 | 5/1939 | Aitken | 132/82 H |
| 2,990,054 | 6/1961 | Gellman | 206/37 R |
| 3,149,188 | 9/1964 | Schmitt | 206/525 |
| 3,800,034 | 3/1974 | Kircher et al. | 424/63 |
| 3,846,556 | 11/1974 | Handjani et al. | 424/364 |
| 3,978,207 | 8/1976 | Fotiu et al. | 424/63 |
| 4,119,712 | 10/1978 | Goldner et al. | 424/63 |
| 4,126,679 | 11/1978 | Davy et al. | 424/63 |

FOREIGN PATENT DOCUMENTS

| | | | |
|---|---|---|---|
| 968535 | 2/1958 | Fed. Rep. of Germany | 424/63 |
| 1492258 | 12/1969 | Fed. Rep. of Germany | 424/63 |
| 2365219 | 7/1974 | Fed. Rep. of Germany | 424/68 |
| 72341 | 9/1973 | Japan | 424/63 |
| 530682 | 4/1977 | U.S.S.R. | 424/81 |

OTHER PUBLICATIONS

Jenkins et al., *The Art of Compounding*, 1957, pp. 367-385, 396-402.

*Primary Examiner*—William T. Dixson, Jr.
*Attorney, Agent, or Firm*—Andrus, Sceales, Starke & Sawall

[57] ABSTRACT

A method of producing a cosmetic product containing an integrally molded powder cake. The product includes a casing having an open top enclosed by a cover, and the casing defines a cavity to contain the powder cake. In fabricating the product, the cover is closed and the casing is inverted and a slurry composed of an inert powdered material, a fatty alcohol and a vaporizable siloxane is introduced into the cavity through an opening in the bottom of the casing. On cooling, the slurry is solidified to form a cake, and subsequently the cake is dried to evaporate the siloxane carrier. The opening in the bottom of the casing can be enclosed by a backing member.

7 Claims, 3 Drawing Figures

METHOD OF PRODUCING A COSMETIC PRODUCT CONTAINING A POWDER CAKE

BACKGROUND OF THE INVENTION

Pressed powders, eye shadow, blushes and face powders currently on the market are produced by compressing loose powder into a metal pan using direct pressure. The pan containing the pressed powder cake is then glued into the compact, which is the primary container.

In the conventional process the pressure used in the pressing operation must be maintained within precise limits. If the pressure is too great, the metal pan may be distorted and must be discarded. In addition, utilizing a high pressure results in a cake which lacks the desired "pay off" characteristics. On the other hand, if the pressure is too low, the pressed cake will lack cohesive strength. Thus, certain powder compositions cannot successfully be used as a pressed powder cake because the pressure required to obtain the necessary cohesive strength will either distort the metal pan or produce a cake that is so hard that it lacks "pay-off".

As a further problem, aerobic bacteria may frequently contaminate the pressed pans, so that the pans must be sterilized before final assembly either by heat or other techniques. This further adds to the cost in producing the pressed powder product.

SUMMARY OF THE INVENTION

The invention is directed to a method of producing a cosmetic product containing a powder composition that is molded directly in the compact or casing without the use of a separate metal pan.

The cosmetic product or compact is composed of a casing having an open top which is enclosed by a hinged cover. The casing defines a cavity to receive the powder composition.

In fabricating the product, the cover is closed and the casing is inverted. A slurry composed of finely divided or powdered inert materials, a fatty alcohol and a volatile siloxane is introduced through an opening in the bottom of the casing to fill the cavity. On cooling, the slurry solidifies to form a cake and subsequently, the siloxane is evaporated, preferably by placing the compact in a drying oven. As the siloxane evaporates the fatty alcohol will migrate toward the exposed surface of the powder composition. The migration of the fatty alcohol results in an increased concentration of the fatty alcohol at the rear exposed surface of the powder cake which adds strength and support to the final product.

After drying, a bottom plate or label can be applied to the bottom of the casing over the exposed surface of the cake.

With the method of the invention, the powder cake is formed directly in the compact without the use of a metal pan, as has been required with prior art methods. By eliminating the use of the metal pan, the design configurations of the cake are greatly increased because the configurations are not restricted to the design of the metal pan.

The invention also provides a substantial cost reduction since the metal pans are eliminated and the labor and assembly operations are also greatly reduced.

By using the slurry technique for forming the powder cake, finely divided materials, not capable of being successfully compressed, can be used to form the cake.

The micro-biological problems are minimized by the invention, since the product is poured and dried at elevated temperatures which discourages microbial contamination. In addition, the only surface of the cake exposed to air is at the bottom of the casing, which is subsequently covered and is never used by the consumer.

Other objects and advantages will appear in the course of the following description.

DESCRIPTION OF THE DRAWINGS

The drawings illustrate the best mode presently contemplated of carrying out the invention.

In the drawings.

DESCRIPTION OF THE PREFERRED EMBODIMENT

Figure 1:
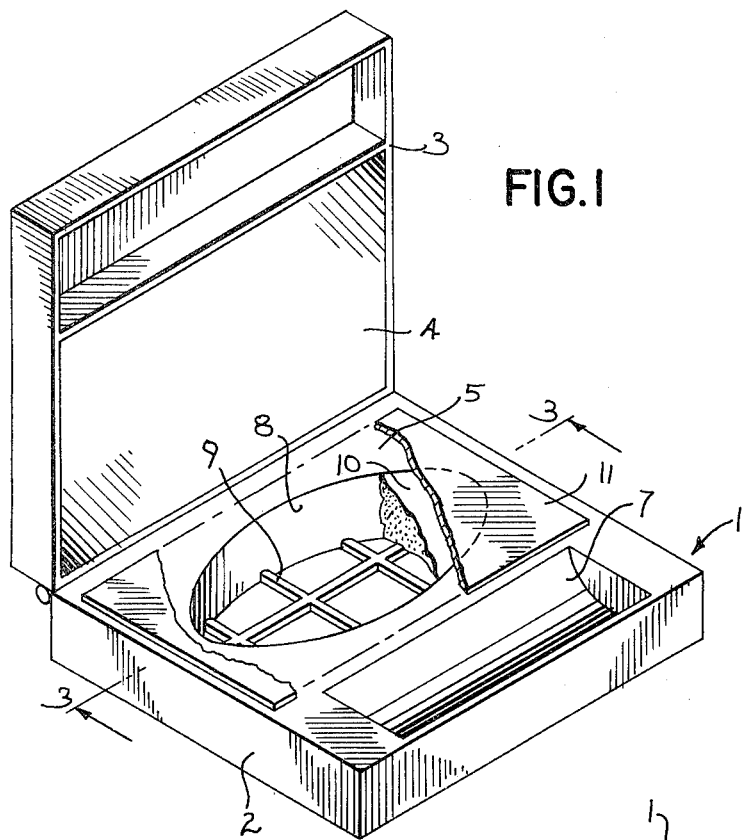
FIG. 1 is a perspective view of a compact to be used in the method of the invention with the cover shown in the open position.
Figure 2:
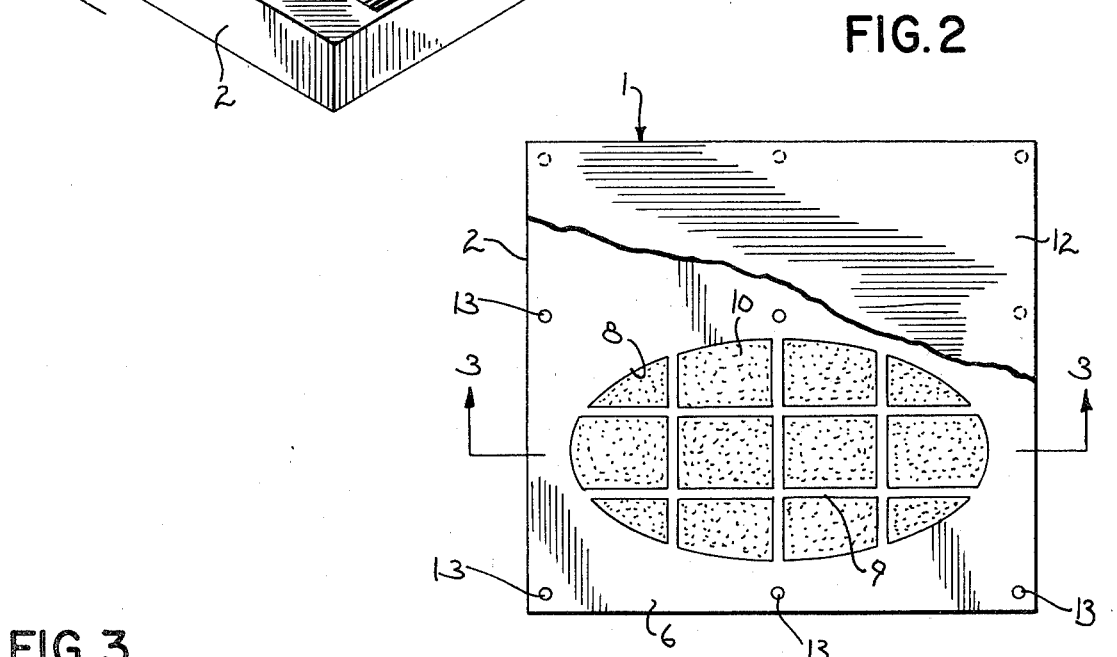
FIG. 2 is a bottom view of the completed compact with parts broken away.
Figure 3:
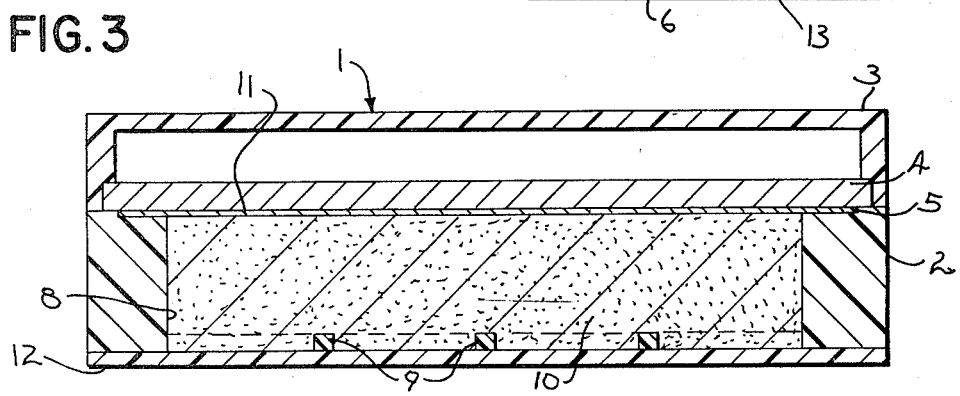
FIG. 3 is a section taken along line 3—3 of FIG. 2.

FIG. 1 illustrates a cosmetic product, such as a compact 1, produced in accordance with the method of the invention. The compact 1 includes a casing 2 and a cover 3 which is hinged to the casing. As shown in FIG. 1, a mirror 4 can be mounted on the underside of the cover.

The casing 2 includes an upper surface 5 and a back surface 6. The upper surface is formed with a shallow tray 7 which normally would receive an applicator, not shown, for applying the powder cake to the skin.

The casing defines a central cavity 8 and a grid 9, which is formed integrally with the back surface 6, extends across the rear portion of the cavity 8. A molded powder cake 10 is disposed within the cavity 8 and extends within the openings in the grid 9.

Mounted over the upper surface of the cake 10 is a purity seal 11 which can be formed of plastic or paper. At the time of use, the purity seal 11 will be removed by the consumer.

The cavity 8 can be closed off on the back surface 6 of the casing, by a back plate 12 which is snapped into place on the back surface 6. As shown in the drawings, the back surface 6 can be provided with a series of outwardly extending projections 13 which are snap fitted within openings in the plate 12. Alternately, a label or small decorative plate can be attached to the back surface 6 over the cavity 8 by an adhesive, as a substitute for the back plate 12, or in some cases, the grid 9 will not be covered and will be exposed.

The powder composition 10 is similar to that described in the copending patent application Ser. No. 945,241, filed Sept. 25, 1978. In general, the powder cake is prepared from a slurry having the following formulation in weight percent:

| | |
|---|---|
| Finely divided inert filler | 70%–10% |
| Fatty alcohol | 5%–30% |
| Volatile siloxane | 25%–60% |
| Cosmetic coloring materials | 1%–35% |

The finely divided filler can take the form of materials such as aluminum hydroxide, koalin, talc, mica, corn starch, calcium carbonate, silicon dioxide, calcined clay, barium sulfate, aluminum oxide, aluminum silicate, and the like.

The fatty alcohols are miscible with the siloxane and serve as a binder for the system and contain from 12 to 22 carbon atoms in the molecule. The fatty alcohol can take the form of cetyl alcohol, stearyl alcohol, and the like.

The volatile siloxane is normally a liquid at room temperature. Chemically it is composed primarily of two cyclic components: D$_4$ cyclodimethicone and D$_5$ cyclodimethicone. The D$_4$ component represents the majority with the D$_5$ being a minor constitutent. Chemically D$_4$ cyclodimethane may be symbolically written as:

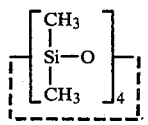

and D$_5$ cyclodimethicone may be symbolically written as:

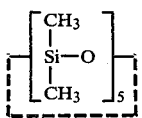

The cosmetically acceptable coloring materials can take the form of titanium dioxide, ferric ferrocyanide or ferric ammonium ferrocyanide, iron oxides, ultramarines, chromium oxide, chromium hydroxide, pearlescents, organic dyes, and lakes.

In addition to the above ingredients, the slurry can also contain small amounts, up to 2% by weight, of a fatty acid ester containing from 12 to 22 carbon atoms, such as iso-propyl myristate or isopropyl palmitate, which prevents dusting of the cake; and/or magnesium stearate which aid in preventing glazing of the cake; and/or a preservative such as methyl paraben or propyl paraben; or perfumes.

To prepare the product of the invention, a purity seal 11 is placed on the upper surface 5 of the casing 2, covering the cavity 8, and the cover 3 is then closed and the compact inverted so that the back surface 5 faces upwardly.

A liquid slurry is then prepared by dispersing the fatty alcohol in the liquid siloxane at a temperature generally in the range of 60° C. to 70° C. The remaining ingredients, such as the powdered filler, coloring materials, and other additives are then mixed into the liquid dispersion to provide the slurry. The slurry, at a temperature in the range of about 50° C. to 60° C., is then poured by gravity into the cavity 8 in the back surface 6 of the compact to fill the cavity and the spaces within the grid. On cooling to a temperature below 45° C., the slurry will solidify to form a solid cake.

Subsequently, the compact is placed in a drying oven at a temperature of about 40° C. for 60 hours to evaporate the siloxane from the cake, so that the dried cake has a residual siloxane content of less than 2% by weight. While it is possible to evaporate the entire siloxane content, it is normally uneconomical to go beyond the 2% level although this can be accomplished by variations in relative humidity and pressure.

During drying, the siloxane will vaporize and the vapor is discharged from the cake through the exposed open bottom of the cavity. The vapor flow will cause a corresponding migration of the fatty alcohol toward the exposed surface, resulting in an increased concentration of the fatty alcohol in the vicinity of the exposed surface. The increased concentration of fatty alcohol will provide greater toughness for the cake in the region of grid 9 to aid in retaining the cake within the cavity.

After drying of the cake to evaporate the siloxane, the plastic bottom plate 12 can be snapped into position and the compact is ready for shipment.

When the consumer opens the compact, the purity seal 11, which serves as a mold for the powder cake 10, is removed and a smooth uniform surface is exposed for use. As the powder cake 10 is molded directly into the compact, it eliminates the use of the conventional metal pan and correspondingly results in a cost reduction.

As the compact is preferably made of molded plastic, the cavity 8 and the molded cake can be formed with a wide variety of configurations which are not possible when using a metal pan, as in the prior art.

By utilizing the slurry technique with the evaporable siloxane carrier, hard-to-press powdered materials can be satisfactorily employed in the cake. The evaporation of the siloxane carrier increases the porosity of the solidified cake, resulting in increased "pay-off" for the cake.

Various modes of carrying out the invention are contemplated as being within the scope of the following claims particularly pointing out and distinctly claiming the subject matter which is regarded as the invention:

We claim:

1. A method of producing a cosmetic product, said product including a casing having a bottom surface and an open top and a cover to enclose the open top, said casing defining a cavity and said bottom surface having an opening communicating with said cavity, comprising the steps of inverting the casing to expose the opening in the bottom surface and positioning the open top against a supporting surface, preparing a liquid slurry containing a finely divided cosmetically acceptable filler and a liquid volatile carrier, introducing the slurry into the opening to substantially fill the cavity and form a molded cake against said supporting surface, evaporating the liquid volatile carrier through said opening to form a dried cake having a molded surface exposed through said opening, and enclosing the open top of the casing with a cover.

2. The method of claim 1, and including the step of positioning a layer of removable sealing material in the cavity against the supporting surface prior to introducing the slurry into the cavity, said slurry being molded against said material, and removing the layer from contact with said molded cake.

3. The method of claim 1, in which the step of evaporating the carrier is accomplished by contacting the molded surface exposed through said opening with a gas while maintaining said molded cake in contact with said supporting surface to thereby evaporate said carrier through said opening.

4. A method of producing a cosmetic product, said product including a casing having a bottom surface and an open top and a cover to enclose the open top, said casing defining a cavity and said bottom surface having an opening communicating with said cavity, comprising the steps of inverting the casing to expose the opening in the bottom surface and positioning the open top against a supporting surface, preparing a liquid slurry comprising a finely divided cosmetically acceptable filler, a fatty alcohol containing 12 to 20 carbon atoms in the molecule and a liquid volatile siloxane, introducing the slurry into the opening to fill the cavity and form a molded cake against said supporting surface, contacting the portion of the molded cake exposed through said opening with a gas while maintaining said molded cake in contact with said supporting surface to thereby evaporate the siloxane and cause a migration of said fatty alcohol towards said exposed portion and providing increased toughness for the cake at said exposed portion.

5. The method of claim 4, and including the step of maintaining the temperature of the slurry in the range of 50° C. to 60° C. when it is introduced into the cavity.

6. A cosmetic product, comprising a casing having a bottom surface and an open top, said casing defining a cavity, a cover to enclose the open top of said casing, the bottom surface of said casing having an opening communicating with said cavity, a grid structure disposed within said opening and dividing said opening into a plurality of apertures, a molded powder cake disposed within the cavity and extending within said apertures in said grid structure, said cake being composed of a mixture of a powdered cosmetic material, a fatty alcohol containing from 12 to 22 carbon atoms in the molecule, cosmetic coloring materials, and a residual amount up to 2% by weight of an evaporable liquid siloxane, the portion of the cake in the region of said grid structure having an increased concentration of said fatty alcohol to provide increased toughness for the cake in said region, and a sheet of sealing material disposed beneath the cover and enclosing the upper surface of said cake.

7. The product of claim 6, and including a backing member disposed on said bottom surface and extending across the opening to cover the same.

* * * * *